Figure 1:
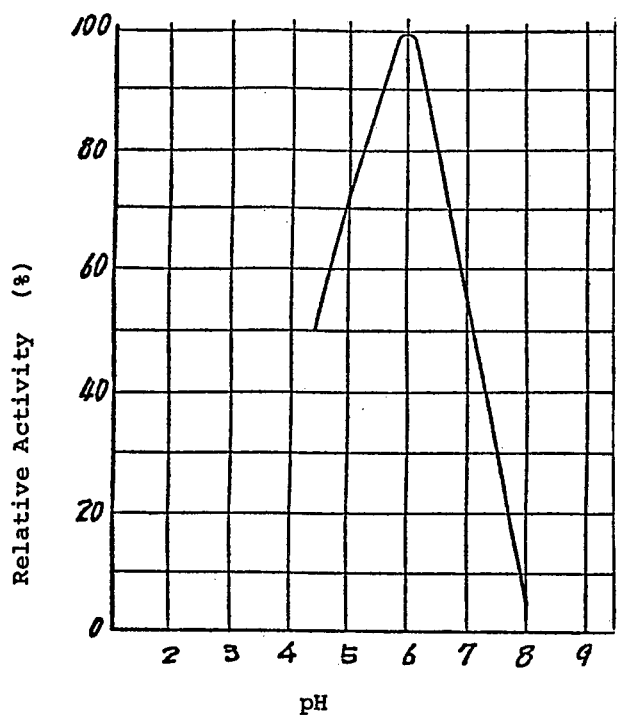
Figure 2:
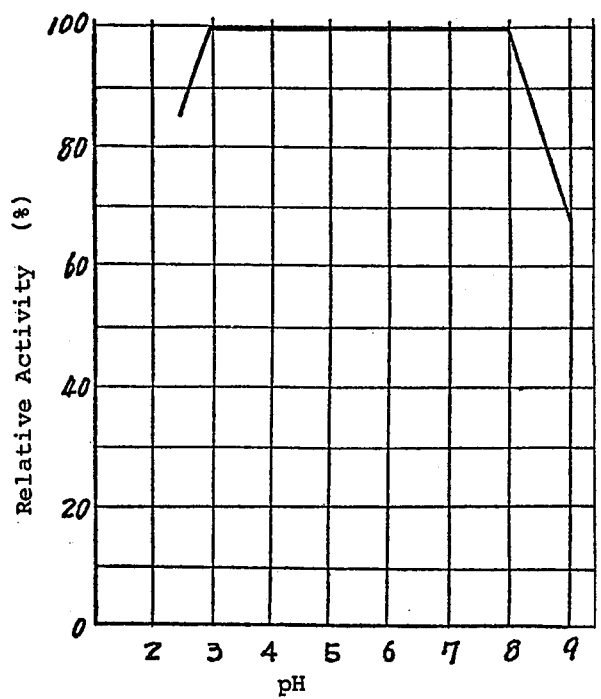
Figure 3:
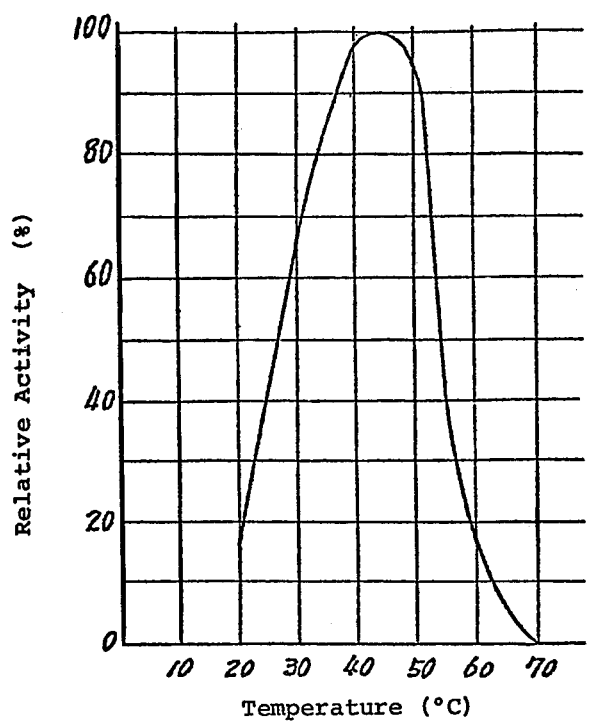
Figure 4:
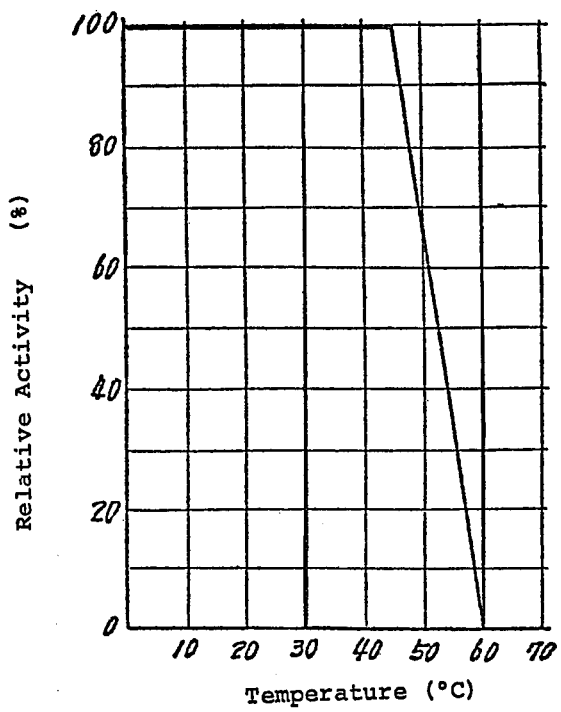

United States Patent [19]

Yokobayashi et al.

[11] 4,102,743

[45] * Jul. 25, 1978

[54] PROCESS FOR THE REMOVAL OF SUCROSE FROM A SUGAR MIXTURE

[75] Inventors: Koji Yokobayashi, Okayama; Tadashi Ikeda, Tokyo; Akira Misaki, Nishinomiya, all of Japan

[73] Assignee: Kabushiki Kaisha Hayashibara Seibutsu Kagaku Kenkyujo, Okayama, Japan

[ * ] Notice: The portion of the term of this patent subsequent to Feb. 7, 1995, has been disclaimed.

[21] Appl. No.: 753,104

[22] Filed: Dec. 21, 1976

[30] Foreign Application Priority Data

Dec. 31, 1975 [JP] Japan ................................ 51-158801

[51] Int. Cl.$^2$ ...................... C12D 13/02; C12D 13/04
[52] U.S. Cl. ........................................ 195/7; 195/11
[58] Field of Search ............... 127/42, 46 R; 195/31 P, 195/96, 4, 7, 11, 31 R; 536/1, 4; 426/7, 48

[56] References Cited

PUBLICATIONS

Ebisu et al., "Studies on the Structures of Polysaccharides (Glucans and Fructans) Produced by Cariogenic Streptococci and on an Enzyme Hydrolyzing the Insoluble Glucan-I. Structural Studies of Insoluble Glucan, Soluble Glucan and Fructans." *Chemical Abstracts*, vol. 85, No. 21, pp. 235, 236 (1976).

Ebisu et al., "The Structure of Water – Insoluble Glucans of Cariogenic Streptococcus Mutans, Formed in the Absence and Presence of Dextranase", *Carbohydrate Research*, vol. 38 (1974), pp. 374–381.

Baird et al., "Investigation of the Polysaccharides Produced by Extra cellular Glycosyltransferases from Streptococcus Mutans," *Chemical Abstracts*, Vol. 77, No. 11, p. 242 (1972).

Jeanes, et al., "Characterization and Classification of Dextrans From Ninety-Six strains of Bacteria," *J. Amer. Chem. Soc.*, vol. 76, No. 20 (1954), pp. 5041–5052.

*Primary Examiner*—Raymond N. Jones
*Assistant Examiner*—Thomas G. Wiseman
*Attorney, Agent, or Firm*—Browdy and Neimark

[57] ABSTRACT

A culture medium composed of necessary sources and tap water is sterilized, inoculated under strains of the genus Streptococcus and then cultivated under aeration and agitation. Subsequent to the cultivation, the resultant was subjected to water-washing and sieving to obtain crude glucan. The crude glucan is then dissolved in NaOH solution and centrifuged. The recovered filtrate is neutralized with HCl and then the insolubilized glucan was collected by centrifugation. After repetition of the procedures, the collected glucan is washed with water thoroughly until no chloride ion is detected in the waste water and then dried to form white purified glucan powder.

4 Claims, 5 Drawing Figures

PROCESS FOR THE REMOVAL OF SUCROSE FROM A SUGAR MIXTURE

The present invention relates to a process for the removal of sucrose from a sucrose-containing sugar mixture.

Today the development of means specifically effective in removing sucrose from sugar mixture is in great damand as evidenced by the need to remove specifically sucrose, which is generally regarded as the cause of inducing formation of dental plaque and caries, from bee honey and in the need for the specific removal of sucrose that inhibits crystallization of raffinose in the production of raffinose from sugar beet molasses.

Despite the demand and needs, no means to remove specifically sucrose from sucrose-containing sugar mixtures of oligo- and mono-saccharides are available. Although chromatography is a known method possible of fractionating various sugars, it is not a method capable of removing specifically sucrose, but is a complicated procedure only for treating smaller amounts of substances, thus is not feasible for industrial practice.

The eager, painstaking research and development for a specific method feasible for removing sucrose from sugar mixture by the present inventors resulted in the invention of a specific method to remove sucrose by allowing water-insoluble glucan which is obtained by cultivating a bacterium of genus Streptococcus capable of producing water-insoluble glucan on a sucrose-containing medium and which possesses water-insoluble-glucan-producing activity to contact with an aqueous solution of a sucrose-containing sugar mixture.

Any bacterium of genus Streptococcus which is capable of producing the water-insoluble glucan from sucrose as specified is employable. One example of an employable bacteria which possesses a high water-insoluble-glucan-producing activity and gives favorable results is Streptococcus salivarius TTL-LP$_1$ FERM-P No. 3310 derived from the saliva of healthy persons. Identification of the strain was carried out by collating its morphological and physiological characteristics with those described in *Bergey's Manual of Determinative Bacteriology*, 8th edition (1974). The results of collation were as follows.

The morphological and physiological characteristics of Streptococcus sp. TTL-LP$_1$ Cells spherical to ovoid with 0.8-1.0 microns in diameter, occurring in pairs or chains of varying length from short to long when grown in liquid media. Non-motile. Endospores not formed. Gram-positive. Not acid-fast.

Agar colonies: Round, smooth, entire to undulate, convex, creamy white, opaque. Punctiform on bouillon agar. About 0.8-1.2 mm in diameter on glucose bouillon agar.

Agar slant: Moist and glistening, slightly raised, creamy white to grayish white, spreading. Growth thin and late on bouillon agar. Growth moderate on glucose bouillon agar.

Broth: Turbid; clear with creamy white to grayish white sediment easily dispersed. No pellicle. Growth weak with light sediment in bouillon. Growth abundant with sediment in glucose bouillon. Final pH range in glucose bouillon broth is 3.8-4.2.

Gelatin stab: No liquefaction. Filiform growth.

Colonies on 5% sucrose and raffinose agar: Produces large mucoid colonies with white, translucent, round, entire, glistening and capitate appearance on raffinose agar, whereas does mucoid colonies with white, translucent, round, entire, smooth, glistening and capitate appearance, becoming large pyramid or conical form colonies with white, translucent, rough, moist and glistening, undulate or angular and cheese-like appearance in old cultures on sucrose agar.

Litmus milk: Acid; coagulated; not peptonized. Reduces litmus only in the bottom of tube without reducing before curdling milk and then oxidizes.

Nitrates not produced from nitrates.

No denitrification.

Methyl red test positive.

Voges-Proskauer test negative.

Indole not produced.

Hydrogen sulfide not produced.

Starch not hydrolyzed.

Citrates not utilized (Koser's and Christensen's citrate media).

Utilizes nitrates, but does not ammonium salts as sole source of nitrogen.

Pigments not formed.

Urea not attacked.

Oxidase not produced.

Catalase not produced.

Acid and gas from carbohydrates: Acid but no gas from glucose, fructose, galactose, sucrose, maltose, lactose, raffinose, trehalose, inulin, inositol and salicin. No acid and gas from glycerol, sorbitol, mannitol, xylose, arabinose and starch.

Predominant end product of glucose fermentation is dextrorotatory lactic acid.

Esculin hydrolyzed.

Hippurates not hydrolyzed.

Does not produce ammonia from arginine.

Beta-hemolytic.

Heat tolerance: Does not survive 60° C for 30 minutes.

NaCl tolerance: Grows in 2% NaCl broth, but does not in 6.5% NaCl broth.

Methylene blue tolerance: Does not grow in 0.1% methylene blue milk.

Bile tolerance: Does not grow on 40% bile blood agar.

Bile solubility negative.

Benzidine test negative.

Growth pH: Optimum, about 7. Grows at pH 5.5–8.0. Does not grow at pH 9.6.

Growth temperature: Optimum, 37° C. Grows at 20°–45° C. Does not grow at 10° or 47° C.

Facultatively anaerobic.

Collation of the following morphological and physiological characteristics with those described in *Bergey's Manual of Determinative Bacteriology*, 8th edition (1974) showed that the strain is bacterium of genus Streptococcus. Chemoorganotrophic; cells do not glide; products of binary fission are equivalent; cells rigidly bound; endospores not formed; gram-positive; do not contain hemocompounds; catalase negative; metabolism of carbohydrates fermentative; predominant end product of glucose fermentation is dextrorotatory lactic acid; and cocci. Furthermore, the following physiological characteristics show that the strain is that of Streptococcus salivarius.

Growth pH, growth temperature; heat tolerance; oxygen demand; NaCl, methylene blue and bile tolerances; bile solubility; hemolysis; hydrolysis of arginine, starch, gelatin, hippurate and esculin; and fermentation of carbohydrates. Based on the observation, the strain was designated as Streptococcus salivarius TTL-LP$_1$ and deposited to the Fermentation Institute, Agency of Industrial Science and Technology, 8-1, 5-Chome, Inagehigashi, Chiba, Japan, which assigned it the FERM-P NO. of 3310.

The water-insoluble glucan used in the invention is prepared by cultivating a bacterium of genus Streptococcus which contains the above strain on a medium containing sucrose as the main carbon source, a nitrogen source, inorganic salts, and other nutrients necessary for the bacterial growth. The culture medium may be in the form of either solid or liquid but a liquid culture medium is generally used. Although the water-insoluble glucan is producible by static cultivation, the agitation and aeration-agitation methods are preferable from view of the higher glucan yield and because they result in a higher glucan-producing activity. Sucrose is most suitable as carbon source for the culture medium in the preparation of the glucan, preferably in the concentration of 1–30%, w/v. Synthetic compounds, such as nitrates, ammonium salts, urea and natural organic substances such as polypeptone, corn steep liquor, yeast extract and amino acids may be used freely as nitrogen source. If necessary, inorganic salts such as phosphates, sulfates, potassium salts, calcium salts, magnesium salts, manganese salts and ferrate are employable. Vitamins, nucleic acids and their analogs may be also added to the culture medium as growth factors. The initial pH, when the microorganism starts growing and producing the glucan, is generally in the range of 6.0–8.0. The cultivation is carried out until maximum glucan production is attained, which usually requires 24 to 96 hours. The glucan is obtained in the forms of such as pellicles, particles, beads and pellets. Moreover, since the culture broth of the water-insoluble glucan and the water-in-soluble glucan hardly exhibit viscosity or tackiness, the formed water-insoluble glucan is separable and recoverable from the culture broth with extreme ease by using such simple means as natural sedimentation, filtration or sieving. The inventors discovered that the water-insoluble glucan, which accumulates in the culture medium, possesses the activity of producing water-insoluble glucan from sucrose, and studied various means to isolate the water-insoluble-glucan-producing substance, but without success. The reason that the isolation attempts resulted unsuccessful may be due to the fact that the water-insoluble-glucan-producing activity present in the crude glucan are attributed to the possible immobilization of glucan-producing enzyme or cells containing the enzyme on the glucan.

The glucan-producing activity was determined as follows. The amount of fructose liberated by reacting a mixture, prepared by adding 0.5 ml of an aqueous suspension of ground crude glucan to 10 ml of a 0.05M phosphate buffer solution pH 6.5, containing 5% sucrose at a temperature of 40° C for 15 minutes, was measured and the activity that liberates one $\mu$ mol of fructose per minute at a temperature of 40° C was designated as one unit. The glucan-producing activity of the crude glucan obtained by cultivation according to the invention is about 0.5–50 units/gram, wet solid basis.

Figure 5:
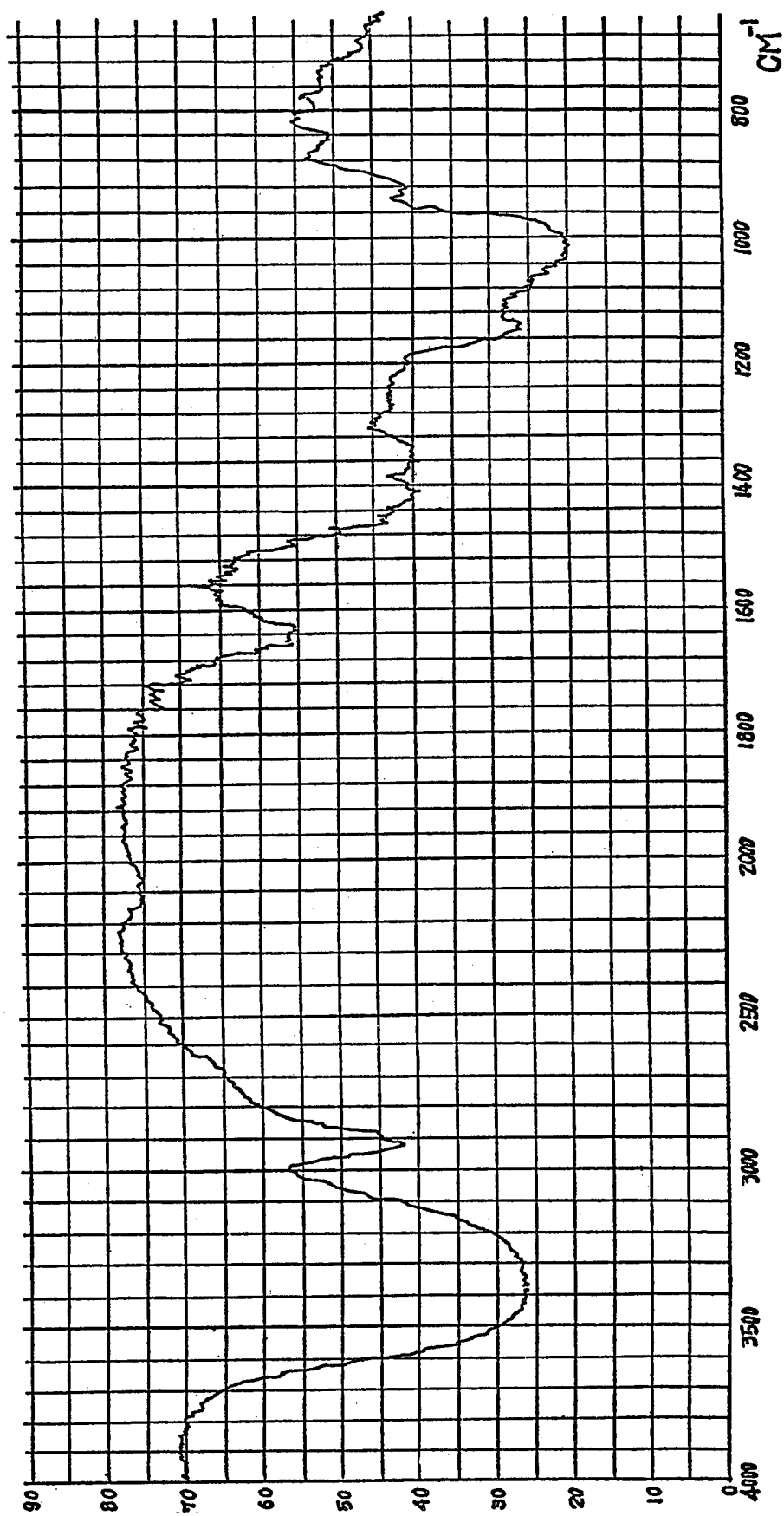

FIGS. 1–4 show the properties of the glucan-producing activity. More particularly, FIGS. 1,2,3 and 4, respectively, show the optimum, pH stability, optimum temperature and heat stability. In FIG. 5 is shown the infrared spectrum of the purified water-insoluble glucan.

The substrate specificity of the glucan-producing activity was investigated with sucrose, maltose, trehalose, isomaltose, maltitol, lactitol, cellobiose, maltulose, turanose, melezitose and melibiose, and the formed fructose or glucose was determined. The results showed that the activity is only specific on sucrose and trehalose and that sucrose is about 50 times more susceptive than trehalose. In order to remove sucrose from the sucrose-containing sugar mixture with the employment of the glucan, an aqueous solution of the sugar mixture is allowed to contact with the glucan to effect reaction therebetween. The process can be carried out by either the batch system wherein the crude glucan is added to an aqueous sucrose solution and effecting reaction of the mixture under occasional agitation, or by a continuous system wherein the crude glucan is packed in a column and allowing an aqueous sucrose solution to pass therethrough.

The preferable conditions for the reaction are; concentration of the sucrose-containing sugar mixture, 1–40%, w/v; pH, 5–7; and temperature, 35–50° C. The employment of glucan-producing activity of 0.5–50 units per gram sucrose present in the sugar mixture is more practical.

By effecting the reaction, sucrose becomes removable specifically from the sugar mixture without affecting the other sugars present in the mixture. The resulting honey from which the sucrose is removed by the process according to the invention still maintains its inherent characteristic flavor and is also an ideal sweetener which has no fears of causing the formation of dental plaque and caries which are regarded as being caused by sucrose.

The process according to the invention can be used in removing the small amount of sucrose that coexists in the sugar mixture, prepared by allowing cyclodextrin glucanotransferase to act on a mixture of sucrose and starch and in which oligoglucosylfructofuranoside and dextrin are the main constituents, with ease. The resulting sucrose-removed sugar mixture may be boiled down into hard candies similarly as corn syrup, or prepared into powder form with ease by drying under reduced pressure or spray-drying. The sucrose-removed product may be, of course, used similarly as regular sugar sweeteners, and also freely as a specialty low-dental-caries-inducing sugar sweetener. In addition, a highly pure raffinose product which has no fears of the crystallization inhibition by sucrose can be prepared from sugar beet molasses from which sucrose is removed beforehand by the process of the invention with great ease and at a high yield. Water-insoluble glucan used in the reaction of the invention was tested in order to confirm its identity as glucan. The results were as follows.

EXPERIMENT 1

Preparation of water-insoluble glucan.

A culture medium comprising polypeptone 0.6%, w/v, sodium acetate 1.0%, w/v, $K_2HPO_4$ 0.05%, w/v, $KH_2PO_4$ 0.05%, w/v, $NH_4Cl$ 0.3%, w/v, yeast extract 0.1%, w/v, $MgSO_4.7H_2O$ 0.5%, w/v, $MnSO_4 .4H_2O$ 0.04%, w/v, sucrose 7%, w/v and tap water was sterilized at 120° C for 15 minutes, inoculated strains of Streptococcus salivarius TTL-LP$_1$ FERM-P NO. 3310 and then cultivated at 35° C for 72 hours under aeration and agitation. Subsequent of the cultivation, the resultant was subjected to water-washing and sieving to obtain crude glucan at a yield of about 43%, d.s.b., against sucrose. The nitrogen and ash contents of the thus obtained crude glucan were respectively 0.25% and 0.17%. The crude glucan was then dissolved in a 1N-NaOH solution and centrifuged at 10,000G for 15 minutes. The recovered filtrate was neutralized with 0.5N-HCl and then the insolubilized glucan was collected by centrifugation. After repetition of the procedures four times, the collected glucan was washed with water thoroughly until not chloride ion was detected in the waste water and then dried to form white purified glucan powder at a yield of about 34%, w/w, d.s.b. against sucrose.

EXPERIMENT 2

Confirmation of the product as glucan.

The confirmation test was carried out with the purified glucan obtained in Experiment 1. The results were as follows:

Purity: No contaminants are detectable on subjection to ultracentrifugation and electrophoresis.
Element analysis: C=40.71%, H=63.1%, N=0%
Ash: Not more than 0.01%
Specific rotation $[\alpha]_D^{25}$ +225° (1=0.5, c=0.5, 1N—NaOH)
Solubility: Dissolves readily in 0.5N-NaOH, slightly in 90% formic acid and dimethyl sulfoxide, and is insoluble in organic solvents such as methanol, acetone and chloroform.
Description: A tasteless, odorless, white fine powder.
Color reaction: Turns into green by the anthrone-sulfuric reaction, and into reddish brown by the indole-hydrogen chloride reaction. Iodine stain, negative.
Ultraviolet spectrum: Shows an absorption at a wavelength of 195 nm or shorter.
Infrared spectrum: Infrared spectrum by the KB$_r$ tablet method is as shown in FIG. 5.
Limiting viscosity number: $[\eta]=2.5$
Sedimentation constant: $S_{20W}=4.9$
Component: The Rf value of paperchromatography of sugar obtained by four-hours hydrolysis with 2N-hydrochloric acid, retention time of gas chromatogram and results of glucose oxidase and peroxidase tests show that the polysaccharide of the present invention contains glucose as its predominant component.
Linkage: Periodate oxidation of methylation, chemical analysis by the Smith degradation or controlled Smith degradation, and enzymatic analysis with iso-maltodextranase give the following results:

From periodate oxidation, the formic acid formation is found as about 0.3 moles per moleglucose residue, and periodate consumption about 0.95 moles per mole glucose residue.

The decomposition products of the methylated glucan, i.e. 2,3,4,6-tetra-O-methyl-D-glucose, 2,4,6-tri-O-methyl-D-glucose, 2,3,4- and 2,3,6-tri-O-methyl-D-glucose, and 2,4-di-O-methyl-D-glucose, are determined quantatively by gas chromatography and mass spectrum, and the molar ratio of the compounds, and molar ratio of the glycerol and erithritol in Smith degradation and controlled Smith degradation are analysed qualitatively and quantitatively by paper- and gas-chromatographies. From the results, the linkage proportions of the glucose residues in the water-insoluble glucan are non-reducing terminal residues, 16.2%; alpha-(1→3)-linkage residues, 36.1%; alpha-(1→6)-linkage residues, 24.9%; alpha-(1→4)-linkage residues, 6.8%; and alpha-(1→3)- and alpha-(1→6)-branched linkages residues 16.0%.

From the fact that if the proportion of non-reducing terminal glucose residues is assigned 2 the above proportions will be approximately 4:3:1:2, the repeated unit of glucose residues in the water-insoluble glucan is assumable as being 12.

In addition, the fact that the isomaltodextranase, derived from a strain of genus Arthrobacter and which liberates isomaltose from the non-reducing terminals of dextran, form a small amount of isomaltose when allowed to act on the water-insoluble glucan indicates that the glucan contains isomaltose structure on its non-reducing terminals.

All-around studies of the results and those of the aforementioned specific rotation and infrared spectrum indicate that alpha-(1→3)-glucosidic linkages are predominantly present in the main chains of the water-insoluble glucan, that one of three glucose residues in the main chain has a branched chain, and that proportion of alpha-(1→4)-glucosidic linkages in the branched chains is about one-third of the alpha-(1→6)-glucosidic linkages.

In other words the glucan produced by the process of the present invention is a novel water-insoluble glucan with high degrees of branching and which is constructed by repeatedly linked units of 12 glucose residues that are mainly linked alpha-(1→3), (1→4) and (1→6).

The present invention will be described in further details with reference to examples.

EXAMPLE 1

One kg of honey with a sucrose content of about 3% was dissolved in 2 liters of water. After adding thereto 200 grams of the wet crude water-insoluble glucan prepared in Experiment 1 (containing above five units of glucan-producing activity per gram), the mixture was allowed to react at a temperature of 40° C for 24 hours with gentle agitation. Subsequent of the reaction, the water-insoluble glucan was filtered out and the resulting filtrate was concentrated to obtain a honey free of sucrose. Paperchromatographic test confirmed that the sucrose was completely removed from the product by the reaction. As to the comparison of the other sugar composition, no changes were hardly noted except the slight increase in the fructose content. In addition, the process did not affect the characteristic flavor inherent to honey. The thus prepared sucrose-free honey can be used as a sweetener which has no fears of causing formation of dental plaque or caries.

In addition, the glucan-producing activity utilized in the reaction showed no decline in activity and was found reusable after water-washing.

EXAMPLE 2

In the resultant mixture, prepared by allowing the cyclodextrin glycanotransferase obtained by cultivation of Bacillus megaterium FERM-P NO. 935 on a mixture of sucrose and a partial hydrolyzate of starch (1:3), coexisted about 10%, w/w, of sucrose.

Fifty liters of a 10%, w/w, aqueous solution of the sugar mixture product was kept at a temperature of 45° C and then was allowed reaction by passage through a column packed with 1.5 kg (wet weight) of the crude water-insoluble glucan obtained in Experiment 1 at a space velocity of about one per hour. Concentration of the resultant yielded a sugar mixture free of sucrose. The sugar compositions of the product prior and after the reaction were compared similarly as in Example 1. The results showed that there were hardly changes except the removal of sucrose and a slight increase of fructose. The sugar mixture product can be used freely in various applications as a sweetener without fears of inducing dental plaque and caries.

EXAMPLE 3

To 10 liters of water was added 1.4 kg of sugar beet molasses and then 800 grams of quick lime in fine powder, and the mixture was stirred for 5 minutes and then filtered. After washing thoroughly the thus obtained residue with cold lime water, the residue was suspended in warm water, 50° C, and then neutralized by blowing therein carbon dioxide gas under agitation conditions, then filtered to obtain a sugar mixture containing sucrose and raffinase. A mixture prepared by adding 1.0 kg (wet weight) of the crude water-insoluble glucan obtained in Experiment 1 to the sugar mixture was allowed reaction at 48° C for 40 hours under gentle agitation conditions. After the water-insoluble glucan content was removed from the reaction mixture by filtration, the resultant concentrated, and crystallized, to yield about 50 grams of a crystalline raffinose product. In comparison with the product of the invention, the yield of the crystalline raffinose from the unreacted sugar mixture was only 9 grams.

What is claimed is:

1. A process for the removal of sucrose from a sugar mixture without substantially affecting the remaining sugar of the mixture, comprising:

contacting an aqueous solution of a sugar mixture containing sucrose with a water-insoluble glucan produced by the process of cultivating *Streptococcus salivarius* TTL-LP$_1$, FERM-P No. 3310, on a sucrose containing medium and separating and recovering the water-insoluble glucan from the resulting culture broth, to effect reaction therebetween thereby forming a water insoluble glucan from the sucrose.

2. A process for the removal of sucrose from a sugar mixture without substantially affecting the remaining sugar of the mixture, comprising:

contacting an aqueous solution of a sugar mixture containing sucrose with a water-soluble glucan composed of non-reducing terminal residues, alpha-(1→3)-linkage residues, alpha-(1→6)-linkage residues, alpha (1→4)-linkage residues, and alpha-(1→3)-and alpha-(1→6)-branched linkage residues in the ratio of 2:4:3:1:2, to effect reaction therebetween thereby forming a water insoluble glucan from the sucrose, said flucan being produced by *Streptococcus salivarius* TTL-LP$_1$, FERM-P No. 3310.

3. A process in accordance with claim 2 wherein said water-insoluble glucan is produced by the process of cultivating *Streptococcus salivarius* TTL-LP$_1$, FERM-P No. 3310, on a sucrose-containing medium and separating and recovering the water-insoluble glucan from the resulting culture broth.

4. A process in accordance with claim 2 further including, prior to said contacting step, the step of:

producing said water-insoluble glucan by cultivating *Streptococcus salivarius* TTL-LP$_1$, FERM-P No. 3310, on a sucrose-containing medium and separating and recovering the water-insoluble glucan from the resulting culture broth, and wherein said water-insoluble glucan in said contacting step is that separated and recovered from said producing step.

* * * * *